US008565887B2

(12) United States Patent
Huang

(10) Patent No.: US 8,565,887 B2
(45) Date of Patent: Oct. 22, 2013

(54) METHOD FOR TREATING PAIN

(75) Inventor: Chung-Shin Huang, Taipei (TW)

(73) Assignee: New Chinese Biotechnology Co., Ltd., Taipei (TW)

( * ) Notice: Subject to any disclaimer, the term of this patent is extended or adjusted under 35 U.S.C. 154(b) by 292 days.

(21) Appl. No.: 12/647,328

(22) Filed: Dec. 24, 2009

(65) Prior Publication Data

US 2010/0100121 A1 Apr. 22, 2010

Related U.S. Application Data

(63) Continuation-in-part of application No. 11/564,844, filed on Nov. 30, 2006, now abandoned.

(30) Foreign Application Priority Data

Dec. 6, 2005 (TW) ................................ 94142932 A

(51) Int. Cl.
*A61N 1/00* (2006.01)

(52) U.S. Cl.
USPC .............................................................. 607/46

(58) Field of Classification Search
USPC .............................................................. 607/46
See application file for complete search history.

(56) References Cited

U.S. PATENT DOCUMENTS

| | | | | |
|---|---|---|---|---|
| 6,393,325 | B1 * | 5/2002 | Mann et al. | 607/46 |
| 6,458,146 | B1 * | 10/2002 | Kramer | 606/204 |
| 2002/0042563 | A1 * | 4/2002 | Becerra et al. | 600/407 |
| 2002/0156101 | A1 * | 10/2002 | Isacsson et al. | 514/317 |
| 2006/0211959 | A1 * | 9/2006 | Oh | 601/15 |
| 2006/0265023 | A1 * | 11/2006 | Blumberg | 607/46 |
| 2008/0300262 | A1 * | 12/2008 | Snutch | 514/255.04 |

* cited by examiner

*Primary Examiner* — Joseph Dietrich
(74) *Attorney, Agent, or Firm* — Thomas Horstemeyer, LLP; Lisa Pavento

(57) ABSTRACT

Disclosed herein is a method of treating pain of a subject. The method is characterized in having the steps of providing treatments not directly onto a pain point, but onto at least one correlative treatment point, to reduce the pain of the subject.

3 Claims, 4 Drawing Sheets

METHOD FOR TREATING PAIN

RELATED APPLICATION

This application is a continuation-in-part of U.S. application Ser. No. 11/564,844, filed on Nov. 30, 2006, now abandoned, which is hereby incorporated by reference as it fully set forth herein.

TECHNICAL FIELD

This disclosure in general relates to a treatment method, and specifically, relates to a method for treating pain of a human.

BACKGROUND ART

According to Chinese medicine, a human body is regulated by meridians, which correspond to energy pathways or nerve bands within a body, and disruption or blockages of such pathways would cause physiological or emotional disharmony.

In Chinese medicine, when a subject feels pain on a specific portion of his/her body, a correlative portion of the body may exhibit a reactive symptom that is probably caused by a functional variation of a meridian or a sympathetic nerve. Providing treatment to the correlative portion of the body having the reactive symptom may ease the pain feeling felt at one specific portion of the body, hence, it is crucial to identify how the one specific portion of the body having the pain feeling is correlated to another portion of the body that may exhibit a reactive symptom.

In view of the above, the inventor of the present disclosure has identified the relationship between a pain point and a correlative treatment point of a human body, hence treatments may be provided to the correlative treatment point, instead of the pain point, to reduce the pain feeling felt by the subject at the pain point of the human body.

SUMMARY

As embodied and broadly described herein, disclosure herein features a method for treating pain, characterized in having the step of providing treatments not directly on a pain point, but on at least one correlative treatment point, which is a correlative body portion of the pain point.

The method includes steps of:

(a) determining a gender, a pain point, a laterality of the pain point, and a character of pain of the subject;

(b) correlating the determined gender, the pain point, the laterality of the pain point, and the character of pain of step (a) with a treatment that is any of a straight treatment or a cross treatment;

(c) finding the at least one correlative treatment point of the pain point;

(d) determining a body portion for the correlative treatment point of step (c), wherein the body portion is selected from the group consisting of head (H), trunk (T), arms (S), forearms (E), hands (W), thighs (L), legs (K) and feet (A); and (e) applying a sufficient force on the determined body portion of the at least one correlative treatment point to reduce the pain of the subject.

According to one embodiment, the character of pain is sthenia syndrome or asthenia syndrome. Step (b) is achieved by rules set forth in Table 2; step (c) is achieved by rules set forth in any of Tables 3a, 3b, 3c or 3d; and in step (d), the body portion is further divided into 10 equal parts. In one example, step (d) is achieved by rules set forth in Table 4a for the straight treatment. In another example, step (d) is achieved by rules set forth in Table 4b for the cross treatment.

The details of one or more embodiments of the invention are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DISCLOSURE OF INVENTION

The practices of this invention are hereinafter described in detail with respect to a method for treating pain. The inventor of the present disclosure has identified that human pain may be more effectively treated by providing treatments not directly onto a pain point, but onto at least one correlative treatment point, of the human body. The correlative treatment, as well as the at least one correlative treatment point of a pain point are determined by rules set forth in this disclosure, particularly, rules set forth in Tables 2 to 4. These rules will be explained in detail in paragraphs below.

It is therefore one aspect of this invention to provide a method for treating pain, which is characterized in providing treatments not on a pain point, but on at least one correlative treatment point. The method comprises steps of:

(a) determining a gender, a pain point, a laterality of the pain point, and a character of pain of the subject;

(b) correlating the determined gender, the pain point, the laterality of the pain point, and the character of pain of step (a) with a treatment that is any of a straight treatment or a cross treatment;

(c) finding the at least one correlative treatment point of the pain point;

(d) determining a body portion for the correlative treatment point of step (c), wherein the body portion is selected from the group consisting of head (H), trunk (T), arms (S), forearms (E), hands (W), thighs (L), legs (K) and feet (A); and (e) applying a sufficient force on the determined body portion of the at least one correlative treatment point to reduce the pain of the subject.

A pain point herein refers to any body part along a particular pair of nerve bands distributed thereof, and such body part has been identified by the subject as having a pain feeling.

Figure 1:
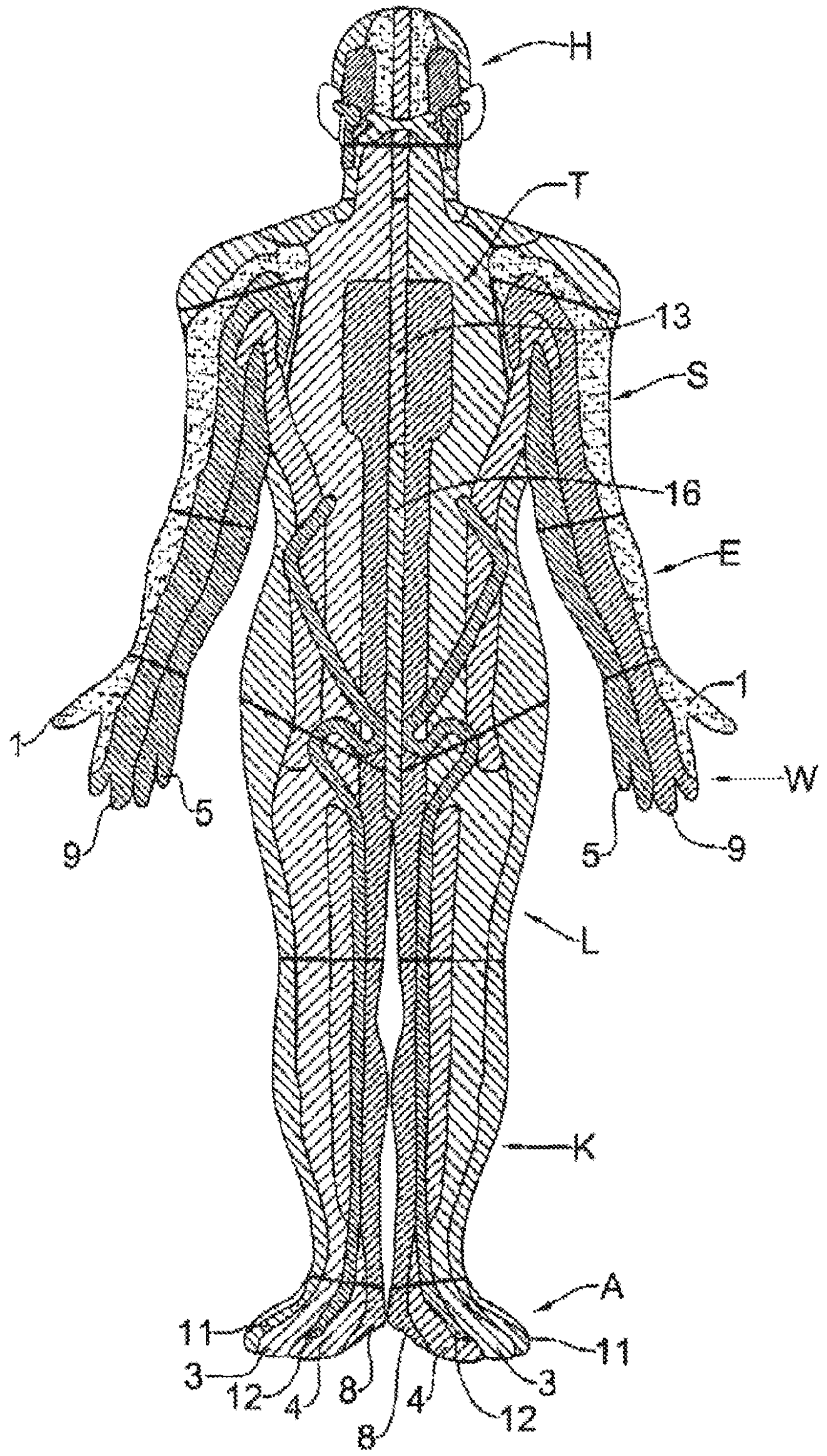
FIG. 1 is the front view of a human body illustrating the twelve pairs of symmetrical nerve bands (1, 2, 3, 4, 5, 6, 7, 8, 9, 10, 11 and 12) and four central nerve bands (13, 14, 15 and 16) according to the distribution of the meridian system in Chinese medicine.
Figure 2:
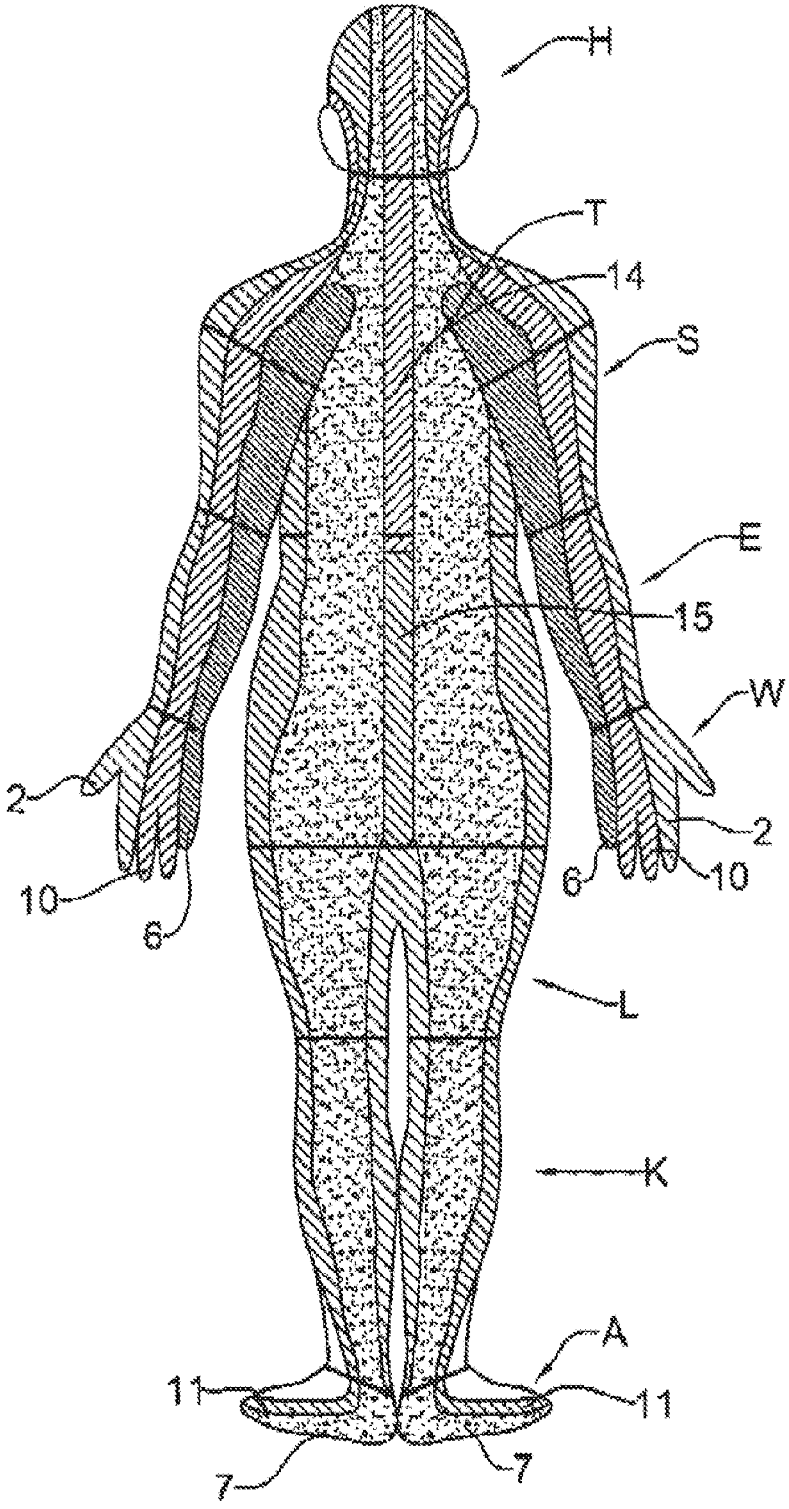
FIG. 2 is the back view of the human body of FIG. 1.

Hence, in present disclosure, a portion of a pair of nerve bands may be used to represent the location of pain point. References are now made to FIGS. 1 and 2, which illustrate twelve pairs of symmetrical nerve bands (1, 2, 3, 4, 5, 6, 7, 8, 9, 10, 11 and 12) and four central nerve bands (13, 14, 15 and 16) of a human body according to the distribution of meridian system of Chinese medicine. These nerve bands (1, 2, 3, 4, 5, 6, 7, 8, 9, 10, 11, 12, 13, 14, 15 and 16) are marked with different oblique lines. The nerve bands are the first (1), second (2), third (3), fourth (4), fifth (5), sixth (6), seventh (7), eighth (8), ninth (9), tenth (10), eleventh (11) and twelfth nerve bands (12), respectively. Each pair of the nerve bands (1, 2, 3, 4, 5, 6, 7, 8, 9, 10, 11 and 12) are formed symmetrically about an axis of the body. Two central nerve bands (14 and 15) correspond respectively to an upper half and a lower half of a governing vessel along a central axis of the body and are termed the fourteenth and fifteenth nerve bands (14 and 15) respectively. The other two central nerve bands (13 and 16) respectively correspond to an upper half and a lower half of a conception vessel and are termed the thirteenth and sixteenth nerve bands (13 and 16). Table 1 summarizes the distribution of the nerve bands (1, 2, 3, 4, 5, 6, 7, 8, 9, 10, 11, 12, 13, 14, 15 and 16).

TABLE 1

| Number | Name | Distribution on the human body |
|---|---|---|
| 1 | First Nerve Band (1) | Distributed Around the Lung Meridian of Hand-Taiyin |
| 2 | Second Nerve Band (2) | Distributed Around the Large Intestine Meridian of Hand-Yangming |
| 3 | Third Nerve Band (3) | Distributed Around the Stomach Meridian of Foot-Yangming |
| 4 | Fourth Nerve Band (4) | Distributed Around the Spleen Meridian of Foot-Taiyin |
| 5 | Fifth Nerve Band (5) | Distributed Around the Heart Meridian of Hand-Shaoyin |
| 6 | Sixth Nerve Band (6) | Distributed Around the Small Intestine Meridian of Hand-Taiyang |
| 7 | Seventh Nerve Band (7) | Distributed Around the Bladder Meridian of Foot-Taiyang |
| 8 | Eighth Nerve Band (8) | Distributed Around the Kidney Meridian of Foot-Shaoyin |
| 9 | Ninth Nerve Band (9) | Distributed Around the Pericardium Meridian of Hand-Jueyin |
| 10 | Tenth Nerve Band (10) | Distributed Around the Triple Warmer Meridian of Hand-Shaoyang |
| 11 | Eleventh Nerve Band (11) | Distributed Around the Gall Bladder Meridian of Foot-Shaoyang |
| 12 | Twelfth Nerve Band (12) | Distributed Around the Live Meridian of Foot-Jueyin |
| 13 | Thirteenth Nerve Band (13) | Distributed Around the Upper Half of the Conception Vessel |
| 14 | Fourteenth Nerve Band (14) | Distributed Around The Upper Half of the Governing Vessel |
| 15 | Fifteenth Nerve Band (15) | Distributed Around the Lower Half of the Governing Vessel |
| 16 | Sixteenth Nerve Band (16) | Distributed Around the Lower Half of the Conception Vessel |

In the present method, a human body is divided into two sides, which are left (L) and right (R) sides, respectively. Hence, the laterality of the pain point herein refers to one particular side of the body where the pain point is located. For example, the laterality of the pain point is left (L) in the case for the pain point located on the left side of the body, and the laterality of the pain point is right (R) in the case for the pain point located on the left side of the body.

The character of pain herein refers to sthenia syndrome or asthenia syndrome. The sthenia syndrome refers to the phenomenon that the subject feels more pain when the pain point is pressured. The asthenia syndrome, on the contrary, refers to the phenomenon that the subject feels less pain when the pain point is pressured.

In step (b), a treatment for the subject is found by correlating the gender, the pain point, the laterality of the pain point, and the character of pain by rules is set forth in Table 2. The treatment may be a straight treatment or a cross treatment, which will be explained in details in paragraphs below.

TABLE 2

| Character of pain | Gender | Laterality | Treatment (treatment point on the ipsilateral side of the body) | Treatment (treatment point on the contralateral side of the body) |
|---|---|---|---|---|
| Sthenia syndrome | male | left | cross | straight |
| | | right | straight | cross |
| | female | left | straight | cross |
| | | right | cross | straight |
| Asthenia syndrome | male | left | straight | cross |
| | | right | cross | straight |
| | female | left | cross | straight |
| | | right | straight | cross |

In step (c), at least one correlative treatment point of the pain point is identified by rules set forth in any of Tables 3a, 3b, 3c or 3d. Similar to the definition provided above for the pain point, a correlative treatment point herein also refers to a body part along a particular pair of nerve bands distributed thereof, and such body part has been identified by the inventor of the present disclosure as a treatment point of a pain point and is suitable for providing treatments thereon to reduce the pain feeling felt by the subject on the pain point. Hence, in present disclosure, a portion of a pair of nerve bands may be used to represent a correlative treatment point of a pain point.

In any of Tables 3a, 3b, 3c or 3d, nerve bands (1, 2, 3, 4, 5, 6, 7, 8, 9, 10, 11, 12, 13, 14, 15 and 16) are correlated in groups. Specifically, the first, second, third, and fourth pairs of nerve bands (1, 2, 3, 4) are grouped together in Table 3a; the fifth, sixth, seventh, and eighth pairs of nerve bands (5, 6, 7, 8) are grouped together in Table 3b; the ninth, tenth, eleventh, and twelfth pairs of nerve bands (9, 10, 11 and 12) are grouped together in Table 3c; and the thirteenth, fourteenth, fifteenth, and sixteenth pairs of nerve bands (13, 14, 15 and 16) are grouped together in Table 3d.

TABLE 3a

| | |
|---|---|
| 1 | 2 |
| 4 | 3 |

TABLE 3b

| | |
|---|---|
| 5 | 6 |
| 8 | 7 |

TABLE 3c

| | |
|---|---|
| 9 | 10 |
| 12 | 11 |

TABLE 3d

| | |
|---|---|
| 13 | 14 |
| 16 | 15 |

With connection to the straight treatment identified in step (b), the straight treatment herein refers to a pain point and a correlative treatment point that are arranged in the same column in any of Tables 3a, 3b, 3c or 3d. In other words, the pain point and its correlative treatment point are positioned in the same column. Taking Table 3a as an example, if a subject identified a body part or a pain point along the first pair of nerve bands (1) distributed thereof, and a straight treatment is required, then the correlative body part where treatments should be provided thereto would be a body part along the fourth pair of nerve bands (4) distributed thereof. Similarly, if a subject identified a body part or a pain point along the second pair of nerve bands (2) distributed thereof, and a straight treatment is required, then the correlative body part where treatments should be provided thereto would be a body part along the third pair of nerve bands (3) distributed thereof.

With connection to the cross treatment identified in step (b), the cross is treatment herein refers to a pain point and a correlative treatment point that are diagonally arranged respectively in the different columns in any of Tables 3a, 3b, 3c or 3d. In other words, the pain point and its correlative treatment point are positioned diagonally to each other in different columns. Taking Table 3a as an example, if a subject identified a body part or a pain point along the first pair of nerve bands (1) distributed thereof, and a cross treatment is required, then the correlative body part where treatments should be provided thereto would be a body part along the third pair of nerve bands (3) distributed thereof. Similarly, if a subject identified a body part or a pain point along the second pair of nerve bands (2) distributed thereof, and a cross treatment is required, then the correlative body part where treatments should be provided thereto would be a body part along the fourth pair of nerve bands (4) distributed thereof.

In step (d), a body portion suitable for providing treatments thereto is identified by rules set forth in Table 4a or 4b. The body portion is correlated with the correlative treatment point identified in step (c), and may be any of the eight different portions of a human body that are divided according to the main joints of the body. These body portions include head (H), trunk (T), a pair of arms (Shoulder, S), a pair of forearms (Elbow, E), a pair of hands (Wrist, W), a pair of thighs (Legs, L), a pair of legs (Knees, K) and a pair of Feet (Ankle, A). Further, the inventor discovered that the upper ends of the first to twelfth nerve bands (1, 2, 3, 4, 5, 6, 7, 8, 9, 10, 11 and 12) are located at the top of the head or the trunk; the upper ends of thirteenth and sixteenth nerve bands (13 and 16) are located at the junction of chest and abdomen of the human body; and the upper ends of the fourteenth and the fifteenth nerve bands (14 and 15) are located at the middle of the back of a human body.

Each body portion such as H, T, S, E, W, L, K or A, may be further divided into 10 equal parts from top to bottom of the body portion, where treatments may be provided to each body part according to rules set forth in Table 4a or 4b. In one example, the body portion or more specifically, the body part of the body portion, of the correlative treatment point is identified by rules set forth in Table 4a for the straight treatment. In another example, the body portion or more specifically, the body part of the body portion, of the correlative treatment point is identified by rules set forth in Table 4b for the cross treatment.

Each pain point and/or its correlative treatment point may be expressed with a set of symbols that is consisted of a body portion (H, T, S, E, W, L, K or A), a first number that represents a pair of nerve bands (1, 2, 3, 4, 5, 6, 7, 8, 9, 10, 11, 12, 13, 14, 15 and 16), and a second number that represents an equal part of the body portion and is any of a number from 1 to 10. The first and the second numbers are respectively presented by a symbol "*", and the two "*" symbols are separated by a symbol ".". Optionally, the set of symbol may further include a fourth symbol representing the laterality (left (L) or right (R)). For example, a symbol T2.8R represents a pain point or a treatment point located at the eighth part of the second nerve band (2) on the right trunk (T) of a body.

TABLE 4a

| Pain Point | Correlative Treatment Point |
|---|---|
| 1 | 4 |
| T1.* | T4.* |
| S1 | L4 |
| S1.* | L4.* |
| E1 | K4 |
| E1.* | K4.* |
| W1 | A4 |
| W1.* | A4.* |
| 2 | 3 |
| H2.* | H3.* |
| T2 | T3 |
| T2.* | T3.* |
| S2 | L3 |
| S2.* | L3.* |
| E2 | K3 |
| E2.* | K3.* |
| W2 | A3 |
| W2.* | A3.* |
| 3 | 2 |
| H3.* | H2.* |
| T3 | T2 |
| T3.* | T2.* |
| L3 | S2 |
| L3.* | S2.* |
| K3 | E2 |
| K3.* | E2.* |
| A3 | W2 |
| A3.* | W2.* |
| 4 | 1 |
| T4.* | T1.* |
| L4 | S1 |
| L4.* | S1.* |
| K4 | E1 |
| K4.* | E1.* |
| A4 | W1 |
| A4.* | W1.* |
| 5 | 8 |
| T5.* | T8.* |
| S5.* | L8.* |
| E5 | K8 |
| E5.* | K8.* |
| W5 | A8 |
| W5.* | A8.* |
| 6 | 7 |
| H6.* | H7.* |
| T6 | T7 |
| T6.* | T7.* |
| S6 | L7 |
| S6.* | L7.* |
| E6 | K7 |
| E6.* | K7.* |
| W6 | A7 |
| W6.* | A7.* |
| 7 | 6 |
| H7.* | H6.* |
| T7 | T6 |
| T7.* | T6.* |
| L7 | S6 |
| L7.* | S6.* |

TABLE 4a-continued

| Pain Point | Correlative Treatment Point |
|---|---|
| K7 | E6 |
| K7.* | E6.* |
| A7 | W6 |
| A7.* | W6.* |
| 8 | 5 |
| T8.* | T5.* |
| L8 | S5 |
| L8.* | S5.* |
| K8 | E5 |
| K8.* | E5.* |
| A8 | W5 |
| A8.* | W5.* |
| 9 | 12 |
| T9.* | T12.* |
| S9 | L12 |
| S9.* | L12.* |
| E9 | K12 |
| E9.* | K12.* |
| W9 | A12 |
| W9.* | A12.* |
| 10 | 11 |
| H10.* | H11.* |
| T10 | T11 |
| T10.* | T11.* |
| S10 | L11 |
| S10.* | L11.* |
| E10 | K11 |
| E10.* | K11.* |
| W10 | A11 |
| W10.* | A11.* |
| 11 | 10 |
| H11.* | H10.* |
| T11 | T10 |
| T11.* | T10.* |
| L11 | S10 |
| L11.* | S10.* |
| K11 | E10 |
| K11.* | E10.* |
| A11 | W10 |
| A11.* | W10.* |
| 12 | 9 |
| T12.* | T9.* |
| L12 | S9 |
| L12.* | S9.* |
| K12 | E9 |
| K12.* | E9.* |
| A12 | W9 |
| A12.* | W9.* |
| 13 | 16 |
| T13.* | T16.* |
| H13.* | T16.10 |
| 14 | 15 |
| T14.* | T15.* |
| H14.* | T15.10 |
| 15 | 14 |
| T15.* | T14.* |
| 16 | 13 |
| T16.* | T13.* |

TABLE 4b

| Pain Point | Correlative Treatment Point |
|---|---|
| 1 | 3 |
| T1.* | T3.* |
| S1 | L3 |
| S1.* | L3.* |
| E1 | K3 |
| E1.* | K3.* |
| W1 | A3 |
| W1.* | A3.* |
| 2 | 4 |
| H2.* | 4 |
| T2.* | T4.* |
| S2 | L4 |

TABLE 4b-continued

| Pain Point | Correlative Treatment Point |
|---|---|
| S2.* | L4.* |
| E2 | K4 |
| E2.* | K4.* |
| W2 | A4 |
| W2.* | A4.* |
| 3 | 1 |
| H3.* | 1 |
| T3 | 1 |
| T3.* | T1.* |
| L3 | S1 |
| L3.* | S1.* |
| K3 | E1 |
| K3.* | E1.* |
| A3 | W1 |
| A3.* | W1.* |
| 4 | 2 |
| T4.* | T2.* |
| L4 | S2 |
| L4.* | S2.* |
| K4 | E2 |
| K4.* | E2.* |
| A4 | W2 |
| A4.* | W2.* |
| 5 | 7 |
| T5.* | T7.* |
| S5 | L7 |
| S5.* | L7.* |
| E5 | K7 |
| E5.* | K7.* |
| W5 | A7 |
| W5.* | A7.* |
| 6 | 8 |
| H6.* | 8 |
| T6.* | T8.* |
| S6 | L8 |
| S6.* | L8.* |
| E6 | K8 |
| E6.* | K8.* |
| W6 | A8 |
| W6.* | A8.* |
| 7 | 5 |
| H7.* | 5 |
| T7 | 5 |
| T7.* | T5.* |
| L7 | S5 |
| L7.* | S5.* |
| K7 | E5 |
| K7.* | E5.* |
| A7 | W5 |
| A7.* | W5.* |
| 8 | 6 |
| T8.* | T6.* |
| L8 | S6 |
| L8.* | S6.* |
| K8 | E6 |
| K8.* | E6.* |
| A8 | W6 |
| A8.* | W6.* |
| 9 | 11 |
| T9.* | T11.* |
| S9 | L11 |
| S9.* | L11.* |
| E9 | K11 |
| E9.* | K11.* |
| W9 | A11 |
| W9.* | A11.* |
| 10 | 12 |
| H10.* | 12 |
| T10.* | T12.* |
| S10 | L12 |
| S10.* | L12.* |
| E10 | K12 |
| E10.* | K12.* |
| W10 | A12 |
| W10.* | A12.* |
| 11 | 9 |
| H11.* | 9 |
| T11.* | T9.* |

TABLE 4b-continued

| Pain Point | Correlative Treatment Point |
|---|---|
| L11 | S9 |
| L11.* | S9.* |
| K11 | E9 |
| K11.* | E9.* |
| A11 | W9 |
| A11.* | W9.* |
| 12 | 10 |
| T12.* | T10.* |
| L12 | S10 |
| L12.* | S10.* |
| K12 | E10 |
| K12.* | E10.* |
| A12 | W10 |
| A12.* | W10.* |
| 13 | 15 |
| T13.* | T15.* |
| H13.* | T15.10 |
| 14 | 16 |
| T14.* | T16.* |
| H14.* | T16.10 |
| 15 | 13 |
| T15.* | T13.* |
| 16 | 14 |
| T16.* | T14.* |

Once the at least one correlative treatment point is identified according to rules set forth above, then a treatment may be provided to the identified correlative treatment point in step (e). The phase “providing treatment” herein refers to applying sufficient force or pressure to the identified correlative treatment point(s) for a sustained period of time. For example, a force of about 0.5-101b may be applied intermittently on the identified correlative treatment point, for a period of about 2-10 minutes. The applied pressure is usually in the range of the pain threshold of the subject, but does not exceed the pain to tolerance of the subject. A skilled therapist including physician and/or a trained technician may be able to determine suitable pressure, way of applying the pressure, as well as the length of the time of the applied pressure, depending on the sex, age, weight, particular body portion that is sensitive to pain and/or the history of the subject without undue experimentation. The pain symptoms felt by the subject at the pain point may be significantly reduced after treatment.

The following Examples are provided to illustrate certain aspects of the present invention and to aid those of skilled in the art in practicing this invention. These Examples are in no way to be considered to limit the scope of the invention in any manner.

EXAMPLES

Example 1

Figure 3:
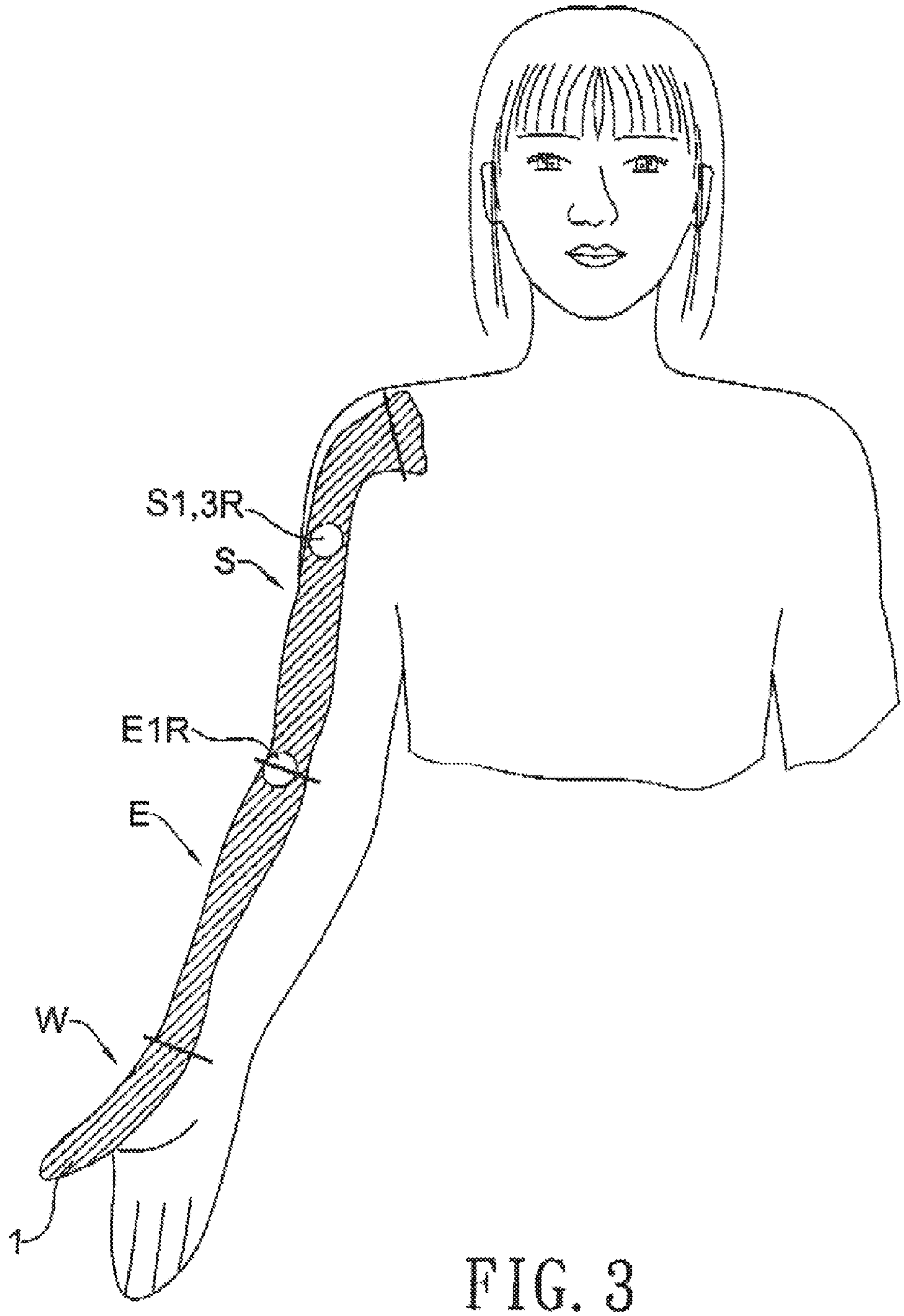
FIG. 3 illustrates the pain point and the identified correlative treatment points of a female subject in accordance with the examples of this invention.
Figure 4:
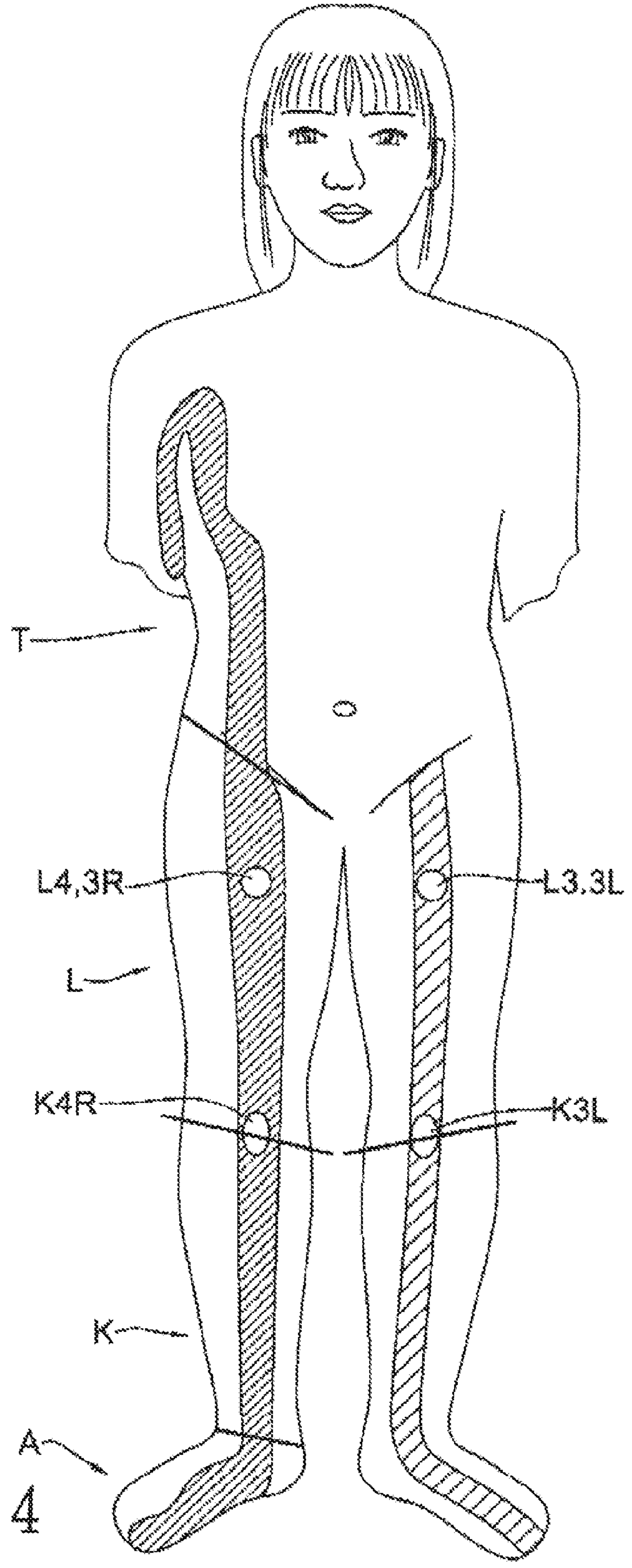
FIG. 4 illustrates the pain point and the identified correlative treatment points of a female subject in accordance with the examples of this invention.

A female subject indicated a pain point on the right elbow of the first nerve band, which was expressed as a set of symbols of E1R, as depicted in FIG. 3. The character of the pain was asthenia syndrome. A first correlative treatment point of the E1R pain point was identified by rules set forth in Tables 2, 3a and 4a, which was on the fourth nerve band (4) of the right knee (i.e., K4R) on the ipsilateral side of the body. A second correlative treatment point of the E1R pain point was identified by rules set forth in Tables 2, 3a and 4b, which was on the third nerve band (3) of the left knee (i.e., K3L) on the contralateral side of the body. The identified correlative treatment points are illustrated in FIG. 4.

Example 2

A female subject indicated a pain point on the first nerve band (1) on the third part of the right upper arm, which was expressed as a set of symbols of S1.3R, as depicted in FIG. 3. The character of the pain was asthenia syndrome. A first correlative treatment point of the S1.3R pain point was identified by rules set forth in Tables 2, 3a and 4a, which was on the fourth nerve band (4) of the third part of the right thigh on the ipsilateral side of the body (i.e., L4.3R). A second correlative treatment point of the S1.3R pain point was identified by rules set forth in Tables 2, 3a and 4b, which was on the third nerve band (3) of the third part of the left thigh on the contralateral side of the body (i.e., L3.3L). The identified correlative treatment points are illustrated in FIG. 4.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for treating pain of a subject characterized in providing treatment not directly onto a pain point, but to at least one correlative treatment point, the method comprises:

(a) determining a gender, the pain point, a laterality of the pain point, and a character of pain of the subject, wherein the character of pain is sthenia syndrome or asthenia syndrome, and the pain point is expressed as at least a body portion at which the pain point is located and a nerve band with which the pain point is associated, wherein the body portion is selected from the group consisting of head (H), trunk (T), arms (S), forearms (E), hands (W), thighs (L), legs (K) and feet (A), and the nerve band is any of the 16 nerve bands set forth in Table 1 and the 16 nerve bands are grouped in accordance with rules set forth in Tables 3a to 3d;

(b) determining whether the treatment is a straight treatment or a cross treatment based on the determined gender, the laterality of the pain point, and the character of pain of step (a), and a laterality of the treatment point in accordance with rules set forth in Table 2;

(c) finding the at least one correlative treatment point of the pain point based on the determined pain point of step (a) and the determined treatment of step (b), wherein the treatment point is expressed as at least a body portion at which the treatment point is located and a nerve band with which the treatment point is associated with, when the treatment is the straight treatment, the at least one correlative treatment point is determined in accordance with rules set forth in Table 4a, and when the treatment is the cross treatment, the at least one correlative treatment point is determined in accordance with rules set forth in Table 4b; and (d) applying a sufficient force on the determined at least one correlative treatment point of step (c) to reduce the pain of the subject.

2. The method of claim 1, wherein each of the body portions is further divided into 10 equal parts from top to bottom, the pain point is further expressed as the part at which the pain point is located, and the at least one correlative treatment point is further expressed as the part at which said treatment point is located.

3. The method of claim 2, wherein the part at which the at least one correlative treatment point is located at a corresponding body part associated with the pain point.

* * * * *